(12) United States Patent
Okino

(10) Patent No.: US 9,273,347 B2
(45) Date of Patent: Mar. 1, 2016

(54) DETECTION OF RNA-INTERACTING REGIONS IN DNA

(75) Inventor: Steven Okino, San Carlos, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 1121 days.

(21) Appl. No.: 13/229,111

(22) Filed: Sep. 9, 2011

(65) Prior Publication Data

US 2012/0082991 A1 Apr. 5, 2012

Related U.S. Application Data

(60) Provisional application No. 61/381,835, filed on Sep. 10, 2010.

(51) Int. Cl.
*C12Q 1/68* (2006.01)

(52) U.S. Cl.
CPC .................................. *C12Q 1/6832* (2013.01)

(58) Field of Classification Search
None
See application file for complete search history.

(56) References Cited

U.S. PATENT DOCUMENTS

| | | |
|---|---|---|
| 5,128,247 A | 7/1992 | Koller |
| 5,972,608 A | 10/1999 | Peterson et al. |
| 6,331,393 B1 | 12/2001 | Laird et al. |
| 6,492,168 B1 | 12/2002 | Kladde et al. |
| 8,652,821 B2 | 2/2014 | Okino et al. |
| 8,728,987 B2 | 5/2014 | Kong et al. |
| 2002/0177139 A1 | 11/2002 | Greenfield et al. |
| 2004/0014086 A1 | 1/2004 | Stamatoyannapoulos et al. |
| 2004/0023206 A1 | 2/2004 | Polansky |
| 2006/0166206 A1 | 7/2006 | Urnov et al. |
| 2007/0009937 A1 | 1/2007 | Laemmli et al. |
| 2009/0130237 A1 | 5/2009 | Cohen |
| 2009/0155791 A1 | 6/2009 | Wojdacz et al. |
| 2009/0215066 A1 | 8/2009 | Ahmed et al. |
| 2009/0286304 A1 | 11/2009 | Latham et al. |
| 2010/0136559 A1 | 6/2010 | Okino et al. |
| 2011/0306042 A1 | 12/2011 | Jouvenot |
| 2012/0064517 A1 | 3/2012 | Okino |
| 2012/0070829 A1 | 3/2012 | Okino et al. |
| 2012/0100597 A1 | 4/2012 | Okino et al. |
| 2012/0208193 A1 | 8/2012 | Okino et al. |
| 2012/0322058 A1 | 12/2012 | Regan et al. |
| 2013/0035239 A1 | 2/2013 | Kong et al. |
| 2013/0109737 A1 | 5/2013 | Young et al. |
| 2014/0220586 A1 | 8/2014 | Kong et al. |

FOREIGN PATENT DOCUMENTS

| | | |
|---|---|---|
| JP | 2002-209588 A | 7/2002 |
| WO | WO 00/29618 | 5/2000 |
| WO | WO 02/097135 | 12/2002 |
| WO | WO 03/004702 | 1/2003 |
| WO | WO 03/035894 | 5/2003 |

(Continued)

OTHER PUBLICATIONS

Ogawa et al. Intersection of the RNA Interference and X-Inactivation Pathways. Science 320:1336-1341; Jun. 6, 2008.*

(Continued)

*Primary Examiner* — Samuel Woolwine
(74) *Attorney, Agent, or Firm* — Weaver Austin Villeneuve & Sampson LLP

(57) ABSTRACT

The present invention provides methods and kits for detecting RNA-interacting regions in genomic DNA.

20 Claims, 1 Drawing Sheet

(56) References Cited

FOREIGN PATENT DOCUMENTS

| WO | WO 03/076949 | 9/2003 |
|---|---|---|
| WO | WO 2006/096727 | 9/2006 |
| WO | WO 2009/061840 | 5/2009 |
| WO | WO 2010/065266 | 6/2010 |
| WO | WO 2012/034007 | 3/2012 |
| WO | WO 2012/034013 | 3/2012 |
| WO | WO 2012/034041 | 3/2012 |
| WO | WO 2012/054613 | 4/2012 |
| WO | WO 2012/112606 | 8/2012 |
| WO | WO 2013/019960 | 2/2013 |
| WO | WO 2015/080966 | 6/2015 |

OTHER PUBLICATIONS

Rivero-Muller, Adolfo et al., "Mixed chelate copper complex, Casiopeina Ilgly®, binds and degrades nucleic acids: A mechanism of cytotoxicity," Chemico-Biological Interactions, Elsevier Science, Ireland (2007) vol. 165, No. 3, pp. 189-199.
Carthew, Richard W. et al., "Origins and Mechanisms of miRNAs and siRNAs," Cell, (2009) vol. 136, No. 4, pp. 642-655.
Rodriguez-Campos, Antonio et al., "RNA is an integral component of chromatin that contributes to its structural organization," PLOS One (2007) vol. 2, No. 11, p. e1182.
Kauffmann et al., "Improvement of RNA secondary structure prediction using RNase H cleavage and randomized oligonucleotides," Nucleic Acids Res. (2009) vol. 37, No. 18, p. e121.
Shiokawa et al., "Stage-specific expression of DNasey during B-cell development and its role in B-cell receptor-mediated apoptosis in WEHI-231 cells," Cell Death Differ. (2007) vol. 14, No. 5, pp. 992-1000.
US Office Action, dated May 31, 2013, issued in U.S. Appl. No. 13/396,496.
US Final Office Action, dated Dec. 5, 2013, issued in U.S. Appl. No. 13/396,496.
US Office Action, dated Sep. 26, 2014, issued in U.S. Appl. No. 13/396,496.
US Final Office Action, dated May 18, 2015, issued in U.S. Appl. No. 13/396,496.
US Restriction Requirement, dated Jan. 24, 2013, issued in U.S. Appl. No. 13/276,553.
US Office Action, dated Apr. 8, 2013, issued in U.S. Appl. No. 13/276,553.
US Notice of Allowance, dated Oct. 8, 2013, issued in U.S. Appl. No. 13/276,553.
US Office Action, dated Apr. 19, 2012, issued in U.S. Appl. No. 13/229,132.
US Final Office Action, dated Sep. 20, 2012, issued in U.S. Appl. No. 13/229,132.
US Office Action, dated Aug. 29, 2013, issued in U.S. Appl. No. 13/229,132.
US Final Office Action, dated Feb. 5, 2014, issued in U.S. Appl. No. 13/229,132.
US Office Action, dated Sep. 26, 2014, issued in U.S. Appl. No. 13/229,132.
US Final Office Action, dated Feb. 10, 2015, issued in U.S. Appl. No. 13/229,132.
US Office Action, dated Jul. 1, 2015, issued in U.S. Appl. No. 13/229,132.
US Office Action, dated May 24, 2013, issued in U.S. Appl. No. 13/565,464.
US Final Office Action, dated Jan. 9, 2014, issued in U.S. Appl. No. 13/565,464.
US Notice of Allowance, dated Mar. 17, 2014, issued in U.S. Appl. No. 13/565,464.
PCT International Search Report and Written Opinion, dated May 2, 2012, issued in PCT/US2012/025120.
PCT International Preliminary Report on Patentability, dated Aug. 29, 2013, issued in PCT/US2012/025120.
European Search Report, dated Dec. 17, 2014, issued in EP Application No. 12 705 595.2.
PCT International Search Report, dated Mar. 26, 2012, issued in PCT/US2011/050992.
PCT International Preliminary Report on Patentability, dated Mar. 21, 2013, issued in PCT/US2011/050992.
European Extended European Search Report, dated Dec. 12, 2013, issued in EP Application No. 11 824 173.6.
European Office Action, dated Sep. 11, 2014, issued in EP Application No. 11 824 173.6.
Japanese Office Action (Notice of Reasons for Rejection), dated Sep. 7, 2015, issued in JP 2013-528327.
PCT International Search Report, dated Mar. 26, 2012, issued in PCT/US2011/050981.
PCT International Preliminary Report on Patentability and Written Opinion, dated Mar. 21, 2013, issued in PCT/US2011/050981.
European Extended Search Report, dated Feb. 20, 2014, issued in EP 11 824 170.2.
Japanese Office Action, dated Jul. 6, 2015, issued in JP 2013-528325.
PCT International Search Report, dated Oct. 22, 2012, issued in PCT/US2012/049344.
PCT International Preliminary Report on Patentability and Written Opinion, dated Feb. 13, 2014, issued in PCT/US2012/049344.
Chinese First Office Action, dated Dec. 8, 2014, issued in CN 201280038451.3.
Chinese Second Office Action, dated Jun. 24, 2015, issued in CN 201280038451.3.
European Extended European Search Report, dated Feb. 5, 2015, issued in EP Application No. 12 819 299.4.
PCT International Search Report and Written Opinion, dated Feb. 25, 2015, issued in PCT/US2014/066822.
Almeida, (Jan. 6, 2009) "Polymorphisms and DNA methylation of gene TP53 associated with extraaxial brain tumors," *Genet Mol Res.*, 8(1):8-18 (abstract only), 2 pages.
Antequera et al., (Aug. 10, 1990) "High levels of de novo methylation and altered chromatin structure at CpG islands in cell lines," *Cell.* 62(3):503-14.
Arnold et al., (1996) "Thermal unfolding and proteolytic susceptibility of ribonuclease A," *Eur. J. Biochem.*, 237:862-869.
Arup Laboratories, (Jan. 2012) "Septin 9 (*SEPT9*) Methylated DNA Detection by Real-Time PCR," *National Reference Laboratory*, 2 pages.
Barski, (May 2010) "Hypermethylation and transcriptional downregulation of the TIMP3 gene is associated with allelic loss on 22q12.3 and malignancy in meningiomas," *Brain Pathol.*20(3):623-31 (abstract only), 2 pages.
Barton, (Jan. 5, 2010) "Collagen and calcium-binding EGF domains 1 is frequently inactivated in ovarian cancer by aberrant promoter hypermethylation and modulates cell migration and survival," *Br J Cancer.*102(1):87-96 (abstract only), 2 pages.
Bennett, (Apr. 2010) "HPV status-independent association of alcohol and tobacco exposure or prior radiation therapy with promoter methylation of FUSSEL18, EBF3, IRX1, and SEPT9, but not SLC5A8, in head and neck squamous cell carcinomas," *Genes Chromosomes Cancer*,49(4):319-26 (abstract only), 2 pages.
Berdasco, (Dec. 22, 2009) "Epigenetic inactivation of the Sotos overgrowth syndrome gene histone methyltransferase NSD1 in human neuroblastoma and glioma," *Proc Natl Acad Sci USA* 106(51):21830-5 (abstract only), 2 pages.
Boyle et al., (Jan. 25, 2008) "High-Resolution Mapping and Characterization of Open Chromatin across the Genome," *CELL* 132:311-322.
Bryan, (Nov. 13, 2009) "Hypermethylation of the DLC1 CpG island does not alter gene expression in canine lymphoma," *BMC Genet.*,10:73 (abstract only), 2 pages.
Buryanov et al., (2005) "The use of prokaryotic DNA methyltransferases as experimental and analytical tools in modern biology," *Analytical Biochemistry*, Academic Press Inc., New York, 338:1-11.
Chen, (Oct. 22, 2009) "Loss of prostasin (PRSS8) in human bladder transitional cell carcinoma cell lines is associated with epithelial-mesenchymal transition (EMT)," *BMC Cancer*, 9:377 (abstract only), 2 pages.

(56) References Cited

OTHER PUBLICATIONS

Cheng, (Feb. 2010) "Reduced CRYL1 expression in hepatocellular carcinoma confers cell growth advantages and correlates with adverse patient prognosis," *J Pathol.*,220(3):348-60 (abstract only), 2 pages.

Chim, (Dec. 2008) "Gene hypermethylation in multiple myeloma: lessons from a cancer pathway approach," *Clin Lymphoma Myeloma.*, 8(6):331-9 (abstract only), 2 pages.

Clarke et al., (Apr. 2009) "Continuous base identification for single-molecule nanopore DNA sequencing," *Nature Nanotechnology*, 4:265-270.

Darzynkiewicz et al., (Jun. 1992) "Features of Apoptotic Ce!ls Measured by Flow Cytometry," *Cytometry*, 13(8):795-808.

Dingwall et al., (1981) "High sequence specificity of micrococcal nuclease," *Nucleic Acids Research* 9(12):2659-2673.

Djeliova et al., (Jan. 1, 2002) "DNase 1 Sensitive Site in the Core Region of the Human β-globin Origin of Replication," *Journal of Cellular Biochemistry*, 87(3):279-283.

Drouin et al., (Jan. 2009) "Chapitre de livre: In vivo DNA analysis (anglais)," *Methods Mol Biol*, 148:175-219.

Eberhart et al., (1996) "Nuclease Sensitivity of Permeabilized Cells Confirms Altered Chromatin Formation at the Fragile X Locus," *Somatic Cell and Molecular Genetics*, 22(6):435-441.

Eid et al., (Jan. 2, 2009) "Real-Time DNA Sequencing from Single Polymerase Molecules," *Science*, 323:133-138.

Epigenomics 2009 "The Septin 9 test—A simple blood-based test for early detection of colorectal cancer," p. 1-4.

Eurofins. LightCycler Probes for FRET Assays [online] Aug. 29, 2013 [retrieved Jan. 28, 2015]. Available on the internet<https://web.archive.org/web/20130829020418/http://www.eurofinsgenomics.eu/en/dna-ma-oligonucleotides/optimised-application-oligos/qper-probes/lightcycler-probes.aspx>, 1 page.

Fackler et al., (2003) "DNA Methylation of Rassf1A, Hin-1, Rar-β, Cyclin D2 and Twist in in Situ and Invasive Lobular Breast Carcinoma," *Int. J. Cancer*: 107:970-975.

Fackler, (Jun. 1, 2009) "Hypermethylated genes as biomarkers of cancer in women with pathologic nipple discharge," *Clin Cancer Res.*, 15(11):3802-11 (abstract only), 2 pages.

Fatemi et al., (2005) "Footprinting of mammalian promoters: use of a CpG DNA methyltransferase revealing mucleosome positions at a single molecule level," *Nucleic Acids Research*, 33(20):e176, pp. 1-9.

Ferrai et al., (Apr. 27, 2007) A Transcription-dependent Micrococcal Nuclease-resistant Fragment of the Urokinase-type Plasminogen Activator Promoter Interacts with the Enhancer, *The Journal of Biological Chemistry*, 282(17):12537-12546.

Flusberg et al., (Jun. 2010) "Direct detection of DNA methylation during single-molecule, real-time sequencing," *Nature Methods*, 7(6):461-465.

Foltz, (Jul. 23, 2009) "DNA methyltransferase-mediated transcriptional silencing in malignant glioma: a combined whole-genome microarray and promoter array analysis," *Oncogene*,28(29):2667-77 (abstract only), 2 pages.

Fu, (Nov. 2009) "Hypermethylation of APC promoter 1A is associated with moderate activation of Wnt signalling pathway in a subset of colorectal serrated adenomas," *Histopathology*,55(5):554-63 (abstract only), 2 pages.

Genomic imprinting from Wikipedia, the free encyclopedia. Printed on May 24, 2013, [Retrieved at http://en.wikipedia.org/wiki/Genomic imprinting on May 24, 2013], 10 pages.

Götze et al., (Dec. 17, 2009) "ECRG4 is a candidate tumor suppressor gene frequently hypermethylated in colorectal carcinoma and glioma," *BMC Cancer*, 9:447 (abstract only), 2 pages.

Grau et al., (Mar. 2011) "Hypermethylation of apoptotic genes as independent prognostic factor in neuroblastoma disease," *Mol Carcinog.*, 50(3):153-62 (abstract only), 2 pages.

Guldberg et al., (Jun. 2002) "Profiling DNA methylation by melting analysis," *METHODS* 27(2):121-127, Abstract, 1 page.

Hagége et al. (2007) "Quantitative analysis of chromosome conformation capture assays (3C-qPCR)," *Nature Protocols* 2(7):1722-1733.

Hajkova et al., (2002) "DNA-Methylation Analysis by the Bisulfite-Assisted Genomic Sequencing Method," *Methods in Molecular Biology, DNA Methylation Protocols*, 200:143-1540.

Hamilton et al., (Dec. 15, 2009) "ATM regulates a RASSF1A-dependent DNA damage response," *Curr Biol.* 19(23):2020-5 (abstract only), 2 pages.

Hernandez-Munain, C. et al., (Jun. 1998) "Cooperation among Multiple Transcription Factors Is Required for Access to Minimal T-Cell Receptor α-Enhancer Chromatin In Vivo," *Mol. and Cell. Biology*, 18(6):3223-3233.

Huang et al., (Jan. 2010) "Genetic and epigenetic silencing of SCARA5 may contribute to human hepatocellular carcinoma by activating FAK signaling," *J Clin Invest.*, 120(1):223-41 (abstract only), 2 pages.

Hughes et al., (2000) "Widespread aneuploidy revealed by DNA microarray expression profiling," *Nature Genetics*, 25:333-337.

Ignatov et al. (Feb. 2010) "APC promoter hypermethylation is an early event in endometrial tumorigenesis," *Cancer Sci.*, 101(2):321-7 (abstract only), 2 pages.

Indovina et al. (Apr. 2010) "Downregulation and aberrant promoter methylation of p16INK4A: a possible novel heritable susceptibility marker to retinoblastoma," *J Cell Physiol.*, 223(1): 143-50 (abstract only), 2 pages.

Isomoto, (2009) "Epigenetic alterations in cholangiocarcinoma-sustained IL-6/STA T3 signaling in cholangio—carcinoma due to SOCS3 epigenetic silencing," *Digestion*, 79:Suppl 1:2-8 (abstract only), 2 pages.

Jacinto et al., (Jan. 2008) "Methyl-DNA immunoprecipitation (MeDIP): Hunting down the DNA methylome," *Biotechniques*, 44(1):35, 37, 39 passim, 5 pages.

Jessen et al., (2004) "Mapping chromatin structure in vivo using DNA methyltransferases," *METHODS* 33:68-80.

Jha et al., (2010) "Reversal of hypermethylation and reactivation of the RAR~2 gene by natural compounds in cervical cancer cell lines," *Folia Biol* (Praha), 56(5):195-200 (abstract only), 1 page.

Jones et al., (Jun. 2002) "The fundamental role of epigenetic events in cancer," *Nat Rev Genet.* 3(6):415-28.

Kanduri, (Jan. 14, 2010) "Differential genome-wide array-based methylation profiles in prognostic subsets of chronic lymphocytic leukemia," *Blood*,115(2):296-305 (abstract only), 2 pages.

Kang et al., (Jun. 2003) "Role of the Promoter in Maintaining Transcriptionally Active Chromatin Structure and DNA Methylation Patterns In Vivo," *Molecular And Cellular Biology* 23(12):4150-4161.

Katsnelson, (May 2010) "Genomics goes beyond DNA sequence," *Nature*, 465:145.

Kim et al., (Dec. 2009) "Borderline and malignant phyllodes tumors display similar promoter methylation profiles," *Virchows Arch.* 455(6):469-75 (abstract only), 2 pages.

Kitzis et al., (1980) "Localization of Phosphoproteins and of Protein Kinases in Chromatin from Hepatoma Tissue-Cultured Cells," *Eur J Biochem*, 111(1):237-244.

Kladde et al., (Feb. 1994) "Positioned nucleosomes Inhibit Dam methylation in vivo," *PNAS* (USA) 91(4)1361-1365.

Ko et al., (Jan. 1996) "Dioxin-induced CYP1A1 Transcription In Vivo: the Aromatic Hydrocarbon Receptor Mediates Transactivation, Enhancer-Promoter Communication, and Changes in Chromatin Structure," *Molecular and Cellular Biology*, 16(1):430-436.

Ko et al., (Jul. 1997) "Transactivation Domains Facilitate Promoter Occupancy for the Dioxin—Inducible CYP1A1 Gene In Vivo," *Molecular and Cellular Biology*, 17(7):3497-3507.

Kron et al., (2009) "Discovery of novel hypermethylated genes in prostate cancer using genomic CpG island microarrays," *PLoS One*,4(3):e4830 (abstract only), 2 pages.

Kulis et al., (2010) "DNA methylation and cancer," *Advances in Genetics*, 70, 27-56 (Abstract only, 2 pages).

Kuo, M. Tien, (1979) "Studies in Heterochromatin DNA: Accessibility of Late Replicating Heterochromatin DNA in Chromatin to Micrococcal Nuclease Digestion," *Chromosoma* (Berl.) 70:183-194.

Kwabi-Addo et al., (2007) "Age-related DNA methylation changes in normal human prostate tissues," *Clin. Cancer Res.*, 13:3796-3802.

Laurent-Puig et al., (Nov. 2010) "Colorectal oncogenesis," *Bull Cancer*, 97(11):1311-21 (abstract only), 2 pages.

(56) References Cited

OTHER PUBLICATIONS

Lee et al., (2004) "PLP2/A4 interacts with CCR1 and stimulates migration of CCR1-expressing HOS cells," *Biochemical and Biophysical Research Communications*, 324:768-772.

Lewis, Matt "Agarose gel electrophoresis (basic method)," Loading Buffer Recipe from Matt Lewis—Methodbook.net [retrieved on Mar. 28, 2013 at http://www.methodbook.net/dna/agarogel.html#loadingbuff] copyright 2001, 5 pages.

Liu et al., (Jul. 2009) "Methylation status of RASSF1A and DAPK promoter in retinoblastoma," *Zhonghua YanKe Za Zhi.*, 45(7):631-5 (abstract only), 2 pages.

Liu et al., (May 27, 2009) "The 14-3-3sigma gene promoter is methylated in both human melanocytes and melanoma," *BMC Cancer*, 9:162 (abstract only), 2 pages.

Lyn-Cook et al., (Dec. 2010) "Gender differences in gemcitabine (Gemzar) efficacy in cancer cells: effect ofindole-3-carbinol," *Anticancer Res.*30(12):4907-13 (abstract only), 1 page.

Ma et al., (2010) "The relationship between methylation of the Syk gene in the promoter region and the genesis of lung cancer," *Clin Lab.*, 56(9-10):407-16 (abstract only), 2 pages.

Majid et al., (Jan. 1, 2010) "Genistein reverses hypermethylation and induces active histone modifications in tumor suppressor gene B-Cell translocation gene 3 in prostate cancer," *Cancer*, 116(1):66-76 (abstract only), 2 pages.

Martin et al., (Feb. 2010) "Epigenetic regulation of the non-canonical Wnt pathway in acute myeloid leukemia," *Cancer Sci.*101(2):425-32 (abstract only), 2 pages.

Martinez et al., (May 16, 2009) "A microarray-based DNA methylation study of glioblastoma multiforme," *Epigenetics*, 4(4):255-64 (abstract only), 2 pages.

Masson et al. (Jul. 10, 1996) "Conditions favoring RNA polymerase 1 transcription in permeabilized cells," *Exp Cell Res*, 226(1):114-125.

Matarazzo et al., (Oct. 2004) "In vivo analysis of DNA methylation patterns recognized by specific proteins: coupling ChiP and bisulfite analysis," *Biotechniques*, 37(4):666-8, 670, 672-3.

Meijer et al., (1996) "Use of Mitochondrial DNA as a Sensitive and Specific Marker for Localization of Mitochondria in Fractionated Plant Extracts," *Plant Molecular Biology Reporter*, 14(4):353-362.

Mellott et al., (2001) "Cytokine-induced changes in chromatin structure and in vivo footprints in the inducible NOS promoter," *Am. J. Physiol. Lung Cell Mol. Physiol.*, 280:L390-L399.

Melotte et al., (Jul. 1, 2009) "N-Myc downstream-regulated gene 4 (NDRG4): a candidate tumor suppressor gene and potential biomarker for colorectal cancer," *J Natl Cancer Inst.*, 101(13):916-27 (abstract only), 2 pages.

Micard et al., (Jul. 1985) "Purification of RNA-free plasmid DNA using alkaline extraction followed by Ultrogel A2 column chromatography," *Anal Biochem.*, 148(1):121-126, Abstract, 2 pages.

Moncada-Pazos et al., (Aug. 15, 2009) "The ADAMTS12 metalloprotease gene is epigenetically silenced in tumor cells and transcriptionally activated in the stroma during progression of colon cancer," *J Cell Sci.* 122(Pt 16):2906-13 (abstract only), 2 pages.

Morris et al., (Mar. 24, 2011) "Genome-wide methylation analysis identifies epigenetically inactivated candidate tumour suppressor genes in renal cell carcinoma," *Oncogene*,30(12):1390-401 (abstract only), 2 pages.

Muggerud et al., (2010) "Frequent aberrant DNA methylation of ABCB1, FOXC1, PPP2R2B and PTEN in ductal carcinoma in situ and early invasive breast cancer," *Breast Cancer Res*, 12(1):R3, 10 pages.

Narita et al., (Jun. 13, 2003) "Rb-Mediated Geterochromatin Formation and Silencing of E2F Target Genes during Cellular Senescence," *Cell*, 113(6):703-716.

Niklinska et al., (2009) "Prognostic significance of DAPK and RASSF1A promoter hypermethylation in non-small cell lung cancer (NSCLC)," *Folia Histochem Cytobiol.* 47(2):275-80 (abstract only), 2 pages.

Nomoto et al., (Mar. 2010) "Epidermal growth factor-containing fibulin-like extracellular matrix protein 1, EFEMP1, a novel tumor-suppressor gene detected in hepatocellular carcinoma using double combination array analysis," *Ann Surg Oneal.*,17(3):923-32 (abstract only), 2 pages.

Nuovo et al., (Oct. 26, 1999) "In situ detection of the hypermethylation-induced inactivation of the *p16* gene as an early event in oncogenesis," *PNAS USA*, 6(22):12754-9.

Okino et al., (Jul. 1995) "Dioxin Induces Localized, Graded Changes in Chromatin Structure: Implications for *Cyp1A1* Gene Transcription," *Molecular and Cellular Biology*, 15(7):3714-3721.

Okino et al., (2007) "Chromatin Changes on the *GSTP1* Promoter Associated with its Inactivation in Prostate Cancer," *Molecular Carcinogenesis*, 46(10):4839-846.

Okino et al., (Sep. 1998) "Hypoxia-inducible Mammalian Gene Expression Analyzed in Vivo at a TATA-driven Promoter and at an Initiator-driven Promoter," *Journal of Biological Chemistry*, 273(37):23837-23843.

Ozsolak et al., (Feb. 2007) "High-throughput mapping of the chromatin structure of human promoters," *Nature Biotechnology* 25(2):244-249.

Paluszczak et al., (Feb. 2011) "Frequent gene hypermethylation in laryngeal cancer cell lines and the resistance to demethylation induction by plant polyphenols," *Toxicol In Vitro.* 25(1):213-21 (abstract only), 2 pages.

Park et al., (Jan. 2011) "Promoter CpG island hypermethylation during breast cancer progression," *Virchows Arch.*, 458(1):73-84 (abstract only), 2 pages.

Patel et al., (Oct. 1997) "Aberrant Silencing of the CpG Island-Containing Human $O^6$-Methylguanine DNA Methyltransferase Gene Is Associated with the Loss of Nucleosome-Like Positioning," *Molecular and Cellular Biology*, 17(10):5813-5822.

Pfeifer et al., (Jun. 1991) "Chromatin differences between active and inactive X chromosomes revealed by genomic footprinting of permeabilized ceils using DNase 1 and ligation-mediated PCR," *Genes Dev.*, 5(6):1102-1113.

Poetsch et al. (Feb. 2011) "Alterations in the tumor suppressor gene p16(INK4A) are associated with aggressive behavior of penile carcinomas," *Virchows Arch.* 458(2):221-9 (abstract only), 2 pages.

"Properties of Exonucleases and Endonucleases," *New England Biolabs, Inc.* [Retrieved at https://www.neb.com/tools-andresources/selection-charts/properties-of-exonucleases-and-endonucleases on Jul. 17, 2015], 2 pages.

Pulling et al., (Dec. 2009) "Dual promoter regulation of death-associated protein kinase gene leads to differentially silenced transcripts by methylation in cancer," *Carcinogenesis*, 30(12):2023-30 (abstract only), 2 pages.

Qian et al., (Jun. 2011) "Abnormal methylation of GRAF promoter Chinese patients with acute myeloid leukemia," *Leuk Res.*, 35(6):783-6 (abstract only), 2 pages.

QIAquick® Spin Handbook (sold by Qiagen®, published Mar. 2008, 44 pages).

Rao et al., (2001) "Chromatin Remodeling, Measured by a Novel Real-Time Polymerase Chain Reaction Assay, Across the Proximal Promoter Region of the *IL-2* Gene," *Journal of Immunology*, 167:4494-4503.

Röhrs et al., (Oct. 16, 2009) "Hypomethylation and expression of BEX2, IGSF4 and TIMP3 indicative of MLL translocations in acute myeloid leukemia," *Mol Cancer*, 8:86 (abstract only), 2 pages.

Ronai, D. et al., (Jan. 22, 2007) "Detection of chromatin-associated single-stranded DNA in regions targeted for somatic hypermutation," *J. Exp. Med.*, 204(1):181-190.

Sakamoto et al., (Apr. 2010) "MT1G hypermethylation: a potential prognostic marker for hepatoblastoma," *Pediatr Res.*, 67(4):387-93 (abstract only), 2 pages.

Sasahira et al., (Feb. 2011) "Downregulation of runt-related transcription factor 3 associated with poor prognosis of adenoid cystic and mucoepidermoid carcinomas of the salivary gland," *Cancer Sci.*, 102(2):492-7 (abstract only), 2 pages.

Schagdarsurengin et al., (Nov. 16, 2009) "Frequent epigenetic inactivation of RASSF10 in thyroid cancer," *Epigenetics*,4(8):571-6 (abstract only), 1 page.

Sharma et al., (2009) "Prognostic relevance of promoter hypermethylation of multiple genes in breast cancer patients," *Cell Oncol.*,31(6):487-500 (abstract only), 2 pages.

(56) References Cited

OTHER PUBLICATIONS

Steensel et al., (2000) "Identification of in vivo DNA targets of chromatin proteins using tethered Dam methyltransferase," *Nature Biotechnology* 18:424-428.

Steinmann et al., (Dec. 2009) "Frequent promoter hypermethylation of tumor-related genes in head and neck squamous cell carcinoma," *Oncol Rep*.22(6):1519-26 (abstract only), 2 pages.

Stephen et al., (Jan. 2009) "DNA hypermethylation profiles in squamous cell carcinoma of the vulva," *Int J Gynecol Pathol.*, 28(1):63-75 (abstract only), 2 pages.

Syeed et al., (Feb. 10, 2011) "Mutational and promoter hypermethylation status of FHIT gene in breast cancer patients of Kashmir," *Mutat Res.*, 707(1-2):1-8 (abstract only), 2 pages.

Tan et al. (2010) "Manipulation and Isolation of Single Cells and Nuclei," *Methods Cell Biol*, 98:79-96.

Tanguay et al., (1990) "PCR-aided DNaseI footprinting of single copy gene sequences in permeabilized cells," *Nucleic Acids Research*, 18(19):5902.

Tänzer et al., (Feb. 4, 2010) "Performance of epigenetic markers SEPT9 and ALX4 in plasma for detection of colorectal precancerous lesions," *PLoS One*, 5(2):e9061, 6 pages.

Thu et al., (2009) "Methylated DNA Immunoprecipitation," *Journal of Visualized Experiments*, 23 pp. 1-4; [http://www.jove.com/index/Details.stp?Id=935] DOI: 10.3791/935.

Tokuyama, (Dec. 2010) "Aberrant Methylation of Heparan Sulfate Glucosamine 3-*O*-sulfotransferase 2 genes as a biomarker in colorectal cancer," *Anticancer Res.* 30(12):4811-4818.

Tomita et al., (Mar. 2011) "Inhibition of gastric carcinogenesis by the hormone gastrin is mediated by suppression of TFF1 epigenetic silencing," *Gastroenterology*, 140(3):879-91 (abstract only), 2 pages.

Tornaletti et al., (Dec. 1, 1996) "A High-Resolution Analysis of Chromatin Structure Along *p53* Sequences," *Molecular Carcinogenesis*, 17(4):192-201.

Toyota et al., (1999) "CpG island methylator phenotypes in aging and cancer," *Seminars in Cancer Biology*, 9:349-357.

Tung et al., (Apr. 15, 2009) "HAI-2 is epigenetically downregulated in human hepatocellular carcinoma, and its Kunitz domain type 1 is critical for anti-invasive functions," *Int J Cancer.*, 124(8):1811-9 (abstract only), 2 pages.

Wang et al., (Oct. 19, 2009) "CHD5 is down-regulated through promoter hypermethylation in gastric cancer," *J Biomed Sci.* 16:95 (abstract only), 2 pages.

Wojdacz et al., (2007) "Methylation-sensitive high resolution melting (MS-HRM): a new approach for sensitive and high-throughput assessment of methylation," *Nucleic Acids Research*, 35(6):e41, 7 pages.

Wu et al., (Jun. 1, 2010) "Glutamate receptor, ionotropic, kainate 2 silencing by DNA hypermethylation possesses tumor suppressor function in gastric cancer," *Int J Cancer*,126(11):2542-52 (abstract only), 2 pages.

Xu, et al., (Feb. 2011) "BCL2L10 protein regulates apoptosis/proliferation through differential pathways in gastric cancer cells," *J Pathol.* 223(3):400-9 (abstract only), 2 pages.

Yao et al., (Jul. 2011) "Aberrant methylation of CCAAT/enhancer binding protein zeta promoter in acute myeloid leukemia," *Leuk Res.*, 35(7):957-60 (abstract only), 2 pages.

Yoon et al., (Apr. 12, 1996) "Poly(ADP-ribosyl)ation of Histone H1 Correlates with Internucleosomal DNA Fragmentation during Apoptosis," *The Journal of Biological Chemistry*, 271(15):9120-9134.

Yu et al., (May 28, 2009) "TSC-22 contributes to hematopoietic precursor cell proliferation and repopulation and is epigenetically silenced in large granular lymphocyte leukemia," *Blood*, 113(22):5558-67 (abstract only), 2 pages.

Zare et al., (Jan. 17, 2009) "Qualitative analysis of Adenomatous Polyposis Coli promoter: hypermethylation, engagement and effects on survival of patients with esophageal cancer in a high risk region of the world, a potential molecular marker," *BMC Cancer*, 9:24 (abstract only), 2 pages.

Zaret K.S., (1999) "In Vivo Analysis of Chromatin Structure," *Methods in Enzymology, Lnkd-Pubmed*, 304:612-626.

Zhang et al., (1989) "In situ nucleoprotein structure at the SV40 major late promoter: melted and wrapped DNA flank the start site," *Genes and Development*, 3:1814-1822.

Zhang et al., (Nov. 2011) "The neuronal pentraxin II gene (NPTX2) inhibit proliferation and invasion of pancreatic cancer cells in vitro," *Mol Biol Rep.*, 38(8):4903-11 (abstract only), 2 pages.

Zimmermann et al., (2007) "The chromatin structure of the lysozyme GAS41 origin of DNA replication changes during the cell cycle," *Biol. Res.*, 40:185-192.

\* cited by examiner

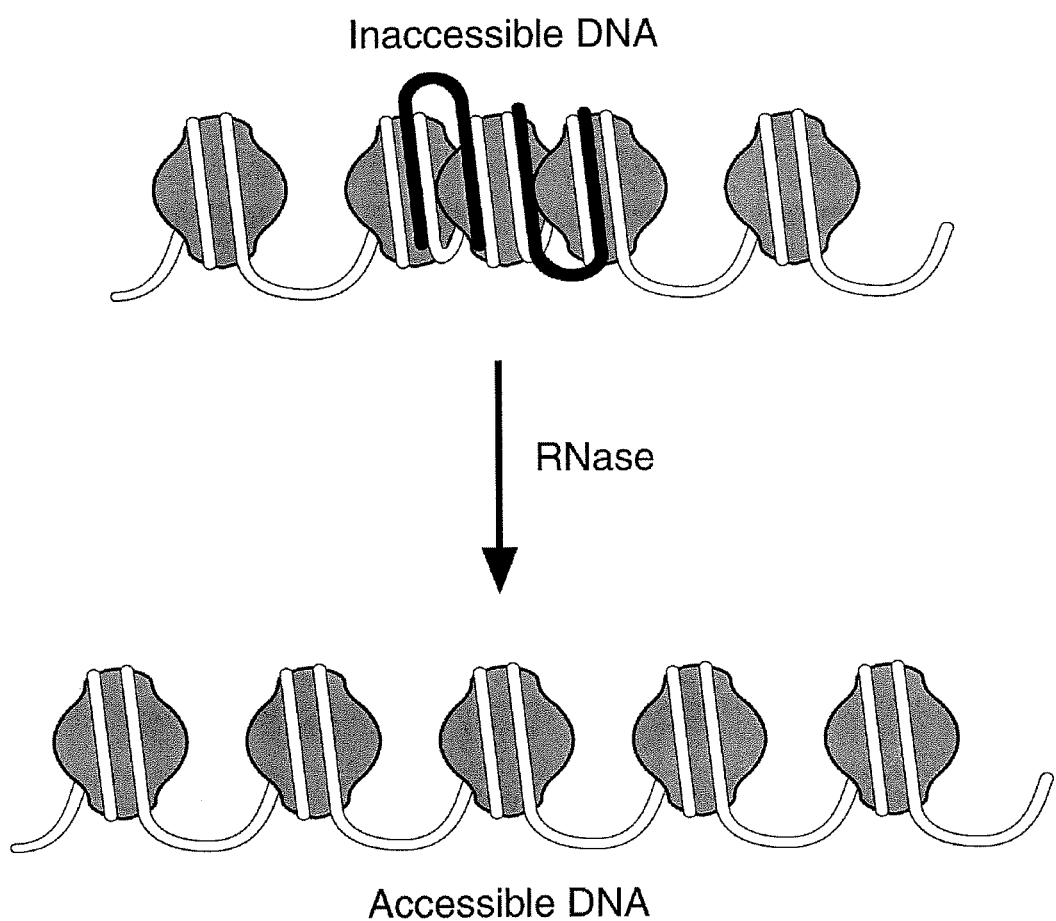

DETECTION OF RNA-INTERACTING REGIONS IN DNA

CROSS REFERENCE TO RELATED PATENT APPLICATIONS

This application claims benefit of priority to U.S. Provisional Patent Application No. 61/381,835, filed Sep. 10, 2010, which is incorporated by reference for all purposes.

BACKGROUND OF THE INVENTION

RNA interaction with genomic DNA is able to influence and regulate the transcription of DNA. Non-coding RNAs such as microRNAs (miRNAs) have been shown to regulate transcription by mediating DNA modification and by changing chromatin structure, such as by changing chromatin from an active state to an inactive state, although in many cases, the mechanisms by which RNA regulate DNA transcription are unknown.

BRIEF SUMMARY OF THE INVENTION

The present invention provides methods of detecting RNA-interacting regions in genomic DNA. In some embodiments, the method comprises:
  introducing an RNA-degrading agent and a DNA-degrading agent into a nucleus, whereby at least one DNA region in the genomic DNA is degraded by the DNA-degrading agent due to the presence of the RNA-degrading agent; and
  detecting the at least one DNA region in the genomic DNA that is degraded by the DNA-degrading agent, wherein an absence or reduction in the quantity of copies of a DNA region indicates that the DNA region is degraded by the DNA-degrading agent; thereby detecting the RNA-interacting regions.

In some embodiments, the DNA-degrading agent is a single-stranded DNA-degrading agent. In some embodiments, the DNA-degrading agent is a double-stranded DNA-degrading agent. In some embodiments, the DNA-degrading agent is an agent that degrades an RNA:DNA duplex.

In some embodiments, the nucleus is in a cell and the RNA-degrading agent and the DNA-degrading agent are introduced into the cell. In some embodiments, the method comprises permeabilizing or disrupting a cell membrane of the cell before or during the introducing step, thereby enhancing introduction of the RNA-degrading agent and/or the DNA-degrading agent into the cell.

In some embodiments, the nucleus is an isolated nucleus and the introducing step comprises introducing the RNA-degrading agent and the DNA-degrading agent into the isolated nucleus. In some embodiments, the RNA-degrading agent is introduced into the nucleus before the DNA-degrading agent is introduced into the nucleus. In some embodiments, the RNA-degrading agent and the DNA-degrading agent are introduced into the nucleus simultaneously.

In some embodiments, the RNA-degrading agent and/or the DNA-degrading agent is a protein. In some embodiments, the RNA-degrading agent and/or the DNA-degrading agent is encoded by a heterologous expression cassette in the cell and the introducing step comprises expressing the agent in the cell.

In some embodiments, the RNA-degrading agent is an RNase. In some embodiments, the RNase is RNase H.

In some embodiments, the DNA-degrading agent is a DNase. In some embodiments, the DNase is S1 nuclease.

In some embodiments, the detecting step comprises nucleotide sequencing or hybridizing a nucleic acid to the at least one DNA region in the genomic DNA that is not degraded. In some embodiments, the detecting step comprises DNA amplification of the at least one DNA region, wherein a region that is refractory to amplification is likely degraded by the DNA-degrading agent. In some embodiments, the DNA amplification comprises a polymerase chain reaction (PCR).

In some embodiments, the genomic DNA is fragmented by the DNA-degrading agent and the method further comprises enriching the DNA for either intact or fragmented DNA and/or size selecting the DNA, wherein intact or relatively larger DNA fragments indicate the relative absence of RNA-interacting regions in the DNA and wherein fragmented or relatively smaller DNA fragments indicate the presence of RNA-interacting regions in the DNA.

The present invention also provides kits comprising:
  a RNA-degrading agent;
  a DNA-degrading agent; and
  a cell membrane permeabilizing or disrupting agent.

In some embodiments, the RNA-degrading agent and/or the DNA-degrading agent is a protein. In some embodiments, the RNA-degrading agent is a RNase. In some embodiments, the RNase is RNase H. In some embodiments, the DNA-degrading agent is a DNase. In some embodiments, the DNase is S1 nuclease.

In some embodiments, the kit comprises a lysolipid cell membrane permeabilizing agent. In some embodiments, the kit further comprises materials for isolating DNA.

DEFINITIONS

An "RNA-interacting region," as used herein, refers to a sequence of genomic DNA with which RNA interacts directly (e.g., by hybridizing to a genomic DNA sequence by canonical Watson-Crick base pairing, or by associating with the major or minor groove of genomic DNA in a triple helix-like structure) or indirectly (e.g., through a mediator such as a protein). In some embodiments, an RNA-interaction region is a region in which an RNA:DNA duplex has formed. As used herein, "RNA" refers to both coding RNA (mRNA) as well as non-coding RNA. Non-limiting examples of non-coding RNA include microRNA (miRNA), small interfering RNA (siRNA), and long non-coding RNA.

An "RNA-degrading agent," as used herein, refers to a molecule that digests or degrades RNA in a detectable manner. In some embodiments, the RNA-degrading agent digests or degrades RNA at a site of RNA-DNA interaction. Exemplary RNA-degrading agents include, but are not limited to, enzymes, proteins, chemicals, and pharmaceutical compounds.

A "DNA-degrading agent," as used herein, refers to a molecule that digests or degrades DNA in a detectable manner. In some embodiments, the DNA-degrading agent digests or degrades DNA at a site of RNA-DNA interaction due to the presence of an RNA-degrading agent that has digested or degraded the RNA at the site of the RNA-DNA interaction. Exemplary DNA-degrading agents include, but are not limited to, enzymes, proteins, chemicals, and pharmaceutical compounds.

A "DNA region," as used herein, refers to a target sequence of interest within genomic DNA. The DNA region can be of any length that is of interest and that interacts with RNA. In some embodiments, the DNA region can include a single base pair, but can also be a short segment of sequence within genomic DNA (e.g., 2-100, 2-500, 50-500 bp) or a larger segment (e.g., 100-10,000, 100-1000, or 1000-5000 bp). The amount of DNA in a DNA region is sometimes determined by the amount of sequence to be amplified in a PCR reaction. For example, standard PCR reactions generally can amplify between about 35 to 5000 base pairs.

The number of copies of a DNA region can be measured and quantified for a sample of interest. The number of copies of the DNA region can be quantified as an actual number of copies or as relative to a control value. For determining whether the number of copies of a DNA region in a sample is relatively "increased," "reduced," or "absent," the number of copies of the DNA region in the sample is quantitated according to any method known in the art (e.g., quantitative PCR) and compared to the number of copies of the DNA region that is present in a control sample. The quantity of copies of a DNA region is "increased" in a sample when the number of copies of the DNA region is greater than the number of copies of the DNA region in the control by at least about 5%, 10%, 15%, 20%, 30%, 40%, 50%, 60%, 70%, 80%, 90%, or more. The quantity of copies of a DNA region is "reduced" in a sample when the number of copies of the DNA region is decreased relative to the number of copies of the DNA region in the control by at least about 5%, 10%, 15%, 20%, 30%, 40%, 50%, 60%, 70%, 80%, 90%, or more. A DNA region is "absent" when the number of copies of the DNA in the sample is below a detectable level.

"Permeabilizing" a cell membrane, as used herein, refers to reducing the integrity of a cell membrane to allow for entry of an RNA- or DNA-degrading agent into the cell. A cell with a permeabilized cell membrane will generally retain the cell membrane such that the cell's structure remains substantially intact. In contrast, "disrupting" a cell membrane, as used herein, refers to reducing the integrity of a cell membrane such that the cell's structure does not remain intact. For example, contacting a cell membrane with a nonionic detergent will remove and/or dissolve a cell membrane, thereby allowing access of an RNA- or DNA-degrading agent to genomic DNA that retains at least some chromosomal structure.

The terms "oligonucleotide" or "polynucleotide" or "nucleic acid" interchangeably refer to a polymer of monomers that can be corresponded to a ribose nucleic acid (RNA) or deoxyribose nucleic acid (DNA) polymer, or analog thereof. This includes polymers of nucleotides such as RNA and DNA, as well as modified forms thereof, peptide nucleic acids (PNAs), locked nucleic acids (LNA™), and the like. In certain applications, the nucleic acid can be a polymer that includes multiple monomer types, e.g., both RNA and DNA subunits.

A nucleic acid is typically single-stranded or double-stranded and will generally contain phosphodiester bonds, although in some cases, as outlined herein, nucleic acid analogs are included that may have alternate backbones, including, for example and without limitation, phosphoramide (Beaucage et al. (1993) Tetrahedron 49(10):1925 and the references therein; Letsinger (1970) J. Org. Chem. 35:3800; Sprinzl et al. (1977) Eur. J. Biochem. 81:579; Letsinger et al. (1986) Nucl. Acids Res. 14: 3487; Sawai et al. (1984) Chem. Lett. 805; Letsinger et al. (1988) J. Am. Chem. Soc. 110: 4470; and Pauwels et al. (1986) Chemica Scripta 26:1419), phosphorothioate (Mag et al. (1991) Nucleic Acids Res. 19:1437 and U.S. Pat. No. 5,644,048), phosphorodithioate (Briu et al. (1989) J. Am. Chem. Soc. 111:2321), O-methylphosphoroamidite linkages (Eckstein, Oligonucleotides and Analogues: A Practical Approach, Oxford University Press (1992)), and peptide nucleic acid backbones and linkages (Egholm (1992) J. Am. Chem. Soc. 114:1895; Meier et al. (1992) Chem. Int. Ed. Engl. 31:1008; Nielsen (1993) Nature 365:566; and Carlsson et al. (1996) Nature 380:207), which references are each incorporated by reference. Other analog nucleic acids include those with positively charged backbones (Denpcy et al. (1995) Proc. Natl. Acad. Sci. USA 92:6097); non-ionic backbones (U.S. Pat. Nos. 5,386,023, 5,637,684, 5,602,240, 5,216,141 and 4,469,863; Angew (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghvi and P. Dan Cook; Mesmaeker et al. (1994) Bioorganic & Medicinal Chem. Lett. 4: 395; Jeffs et al. (1994) J. Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which references are each incorporated by reference. Nucleic acids containing one or more carbocyclic sugars are also included within the definition of nucleic acids (Jenkins et al. (1995) Chem. Soc. Rev. pp 169-176, which is incorporated by reference). Several nucleic acid analogs are also described in, e.g., Rawls, C & E News Jun. 2, 1997 page 35, which is incorporated by reference. These modifications of the ribose-phosphate backbone may be done to facilitate the addition of additional moieties such as labeling moieties, or to alter the stability and half-life of such molecules in physiological environments.

In addition to naturally occurring heterocyclic bases that are typically found in nucleic acids (e.g., adenine, guanine, thymine, cytosine, and uracil), nucleic acid analogs also include those having non-naturally occurring heterocyclic or other modified bases, many of which are described, or otherwise referred to, herein. In particular, many non-naturally occurring bases are described further in, e.g., Seela et al. (1991) Helv. Chim. Acta 74:1790, Grein et al. (1994) Bioorg. Med. Chem. Lett. 4:971-976, and Seela et al. (1999) Helv. Chim. Acta 82:1640, which are each incorporated by reference. To further illustrate, certain bases used in nucleotides that act as melting temperature (Tm) modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil, 5-ethynyluracil; 5-propynyluracil, and the like.

BRIEF DESCRIPTION OF THE DRAWINGS

FIG. 1. Principle of RNA-chromatin interaction. RNA (black) interaction with chromosomal DNA (white) can compact the DNA and make it inaccessible. RNA:DNA interaction may be direct (i.e., base-pairing; interaction in the major or minor DNA groove) or indirect (i.e., through protein intermediates). Treatment of chromatin with RNase can degrade the RNA and make chromosomal regions of RNA:DNA interaction more accessible.

DETAILED DESCRIPTION OF THE INVENTION

I. Introduction

Methods of detecting genomic DNA regions that interact with RNA are provided. The methods involve introducing an RNA-degrading agent and a DNA-degrading agent into a nucleus and then detecting the one or more regions in the genomic DNA that are degraded by the DNA-degrading agent, wherein the one or more regions of the genomic DNA are degraded by the DNA-degrading agent due to the presence of the RNA-degrading agent. Regions of genomic DNA degradation, which may be detected by an absence or reduction in the number of copies of the DNA region or by its inability to be amplified by PCR, likely correspond to genomic DNA regions that interact with RNA.

The methods of the present invention are useful, for example, for any diagnostic, prognostic, or other personalized medicine application where RNA interaction with one or more DNA regions is or may be correlated with a particular disease or condition.

II. General Method

The methods of the invention involve introducing an RNA-degrading agent and a DNA-degrading agent into a nucleus, whereby at least one DNA region of genomic DNA in the nucleus is degraded by the DNA-degrading agent due to the presence of the RNA-degrading agent, and then detecting the at least one DNA region of genomic DNA that is degraded by the DNA-degrading agent.

In some embodiments, the nucleus into which the RNA-degrading agent and/or DNA-degrading agent are introduced is in a cell, and the RNA-degrading agent and/or DNA-degrading agent are introduced into the cell. Alternatively, the RNA-degrading agent and/or DNA-degrading agent are introduced directly into the nucleus of the cell. Alternatively, the nucleus is an isolated nucleus and the RNA-degrading agent and/or DNA-degrading agent are introduced into the isolated nucleus.

The methods of the invention can include permeabilizing or disrupting a cell membrane of the cell, thereby enhancing introduction of the RNA-degrading agent and/or DNA-degrading agent into the cell. The permeabilization or disruption of the cell membrane can occur before the RNA-degrading agent and/or DNA-degrading agent are introduced into the cell, or permeabilization or disruption of the cell membrane can occur simultaneously with the introduction of the RNA-degrading agent and/or DNA-degrading agent.

A variety of eukaryotic cells can be used in the present invention. In some embodiments, the cells are animal cells, including but not limited to, human, or non-human, mammalian cells. Non-human mammalian cells include but are not limited to, primate cells, mouse cells, rat cells, porcine cells, and bovine cells. In some embodiments, the cells are plant or fungal (including but not limited to yeast) cells. Cells can be, for example, cultured primary cells, immortalized culture cells or can be from a biopsy or tissue sample, optionally cultured and stimulated to divide before assayed. Cultured cells can be in suspension or adherent prior to and/or during the permeabilization and/or DNA modification steps. Cells can be from animal tissues, biopsies, etc. For example, the cells can be from a tumor biopsy.

The methods of the invention provide for detecting the one or more DNA regions of the genomic DNA that are degraded by the DNA-degrading agent, wherein an absence of a DNA region or a reduction in the number of copies of a DNA region indicates that the DNA region is degraded by the DNA-degrading agent. A wide variety of methods are known and can be used to detect the absence or reduction in DNA copies of the DNA region, and include but are not limited to, DNA sequencing, PCR amplification to analyze a targeted region, genomic DNA library screening, and size selection of DNA fragments.

The present methods can include correlating degradation of one or more DNA regions of the genomic DNA with RNA interactions with those one or more DNA regions. In some embodiments, RNA interaction with a DNA region correlates with a greater amount of degradation of the DNA region relative to a genomic DNA region that does not interact with RNA. In some embodiments, RNA interaction with a DNA region correlates with an absence of the DNA region following degradation by RNA- and DNA-degrading agents.

III. RNA-Degrading Agents and DNA-Degrading Agents

According to the methods of the present invention, an RNA-degrading agent and a DNA-degrading agent are introduced into a nucleus, or into a cell having a nucleus, and at least one DNA region in genomic DNA in the nucleus is degraded by the DNA-degrading agent due to the presence of the RNA-degrading agent. At sites of RNA-DNA interaction, e.g., a RNA:DNA duplex, the presence of the RNA-degrading agent will result in degradation of the RNA (e.g., the RNA strand in a RNA:DNA duplex), while the presence of the DNA-degrading agent will result in degradation of the DNA (e.g., the DNA strand in a RNA:DNA duplex or a single-stranded DNA following digestion of the RNA that was interacting with the DNA). At sites of RNA:DNA interaction that are not due to base pairing, or at sites where RNA associates with chromatin through protein intermediates but does not physically contact the DNA, degradation of RNA may alter the local chromatin structure and change the accessibility of the DNA-degrading agent to the DNA component of chromatin.

In some embodiments, the RNA-degrading agent and the DNA-degrading agent are introduced into the nucleus or the cell having the nucleus simultaneously. In some embodiments, the RNA-degrading agent is introduced into the nucleus or the cell having the nucleus before the DNA-degrading agent is introduced into the nucleus or the cell having the nucleus.

In some embodiments, the RNA-degrading agent and/or the DNA-degrading agent are introduced into a nucleus or a cell having a nucleus by passive transport, e.g., diffusion or facilitated diffusion. Alternatively, the RNA-degrading agent and/or the DNA-degrading agent can be introduced into a nucleus or a cell having a nucleus through the use of a natural or artificial carrier, transporter, or solvent. The carrier, transporter, or solvent can be any polynucleotide, polypeptide, small molecule, organic compound, or inorganic compound that can facilitate transport of the RNA- and/or DNA-degrading agent through a cell membrane into a nucleus or a cell. In some embodiments, the RNA- and/or DNA-degrading agent is encoded by a heterologous expression cassette (i.e., a nucleic acid construct that is not endogenous to the cell, which when introduced into the cell, results in transcription and/or translation of a RNA or polypeptide, respectively) that is introduced into the cell.

In some embodiments, a cell membrane of a cell into which the RNA-degrading agent and DNA-degrading agent are to be introduced is permeabilized or disrupted in order to enhance introduction of the RNA-degrading agent and/or DNA-degrading agent into the cell. The RNA-degrading agent and/or DNA-degrading agent can be introduced into the cell simultaneously with permeabilization (e.g., during electroporation or during incubation with permeabilizing agent) or following permeabilization (e.g., following removal of the permeabilizing agent, optionally with a change of the buffer). Alternatively, in some embodiments, the RNA-degrading agent and/or DNA-degrading agent is contacted to the genomic DNA without one or more intervening steps (e.g., without an exchange of buffers, washing of the cells, etc.). This latter approach can be convenient for reducing the amount of labor and time necessary and also removes a potential source of error and contamination in the assay.

The quantity of RNA-degrading agent and/or DNA-degrading agent used, as well as the length of time of the reaction with the RNA-degrading agent and/or DNA-degrading agent will depend on the agent used. Those of skill in the art will appreciate how to adjust conditions depending on the agent used. Generally, the conditions of the RNA degrading and/or DNA degrading step are adjusted such that detectable degradation is achieved. "Detectable" degradation, as used herein, refers to contacting the RNA and/or DNA with a degrading agent for sufficient time and under appropriate conditions to allow for cleavage of at least 5% and typically at least 10%, of all of the RNA-DNA interaction sites for the target DNA region of interest. Conditions, including the time, buffers and other reagents necessary for detectable degradation, are typically provided by manufacturers of the degradation agents. Those of skill in the art will recognize that the quality of the sample may inhibit nucleic acid degradation.

A. RNA-Degrading Agents

An RNA-degrading agent of the present invention is any reagent that is capable of cutting, digesting, or degrading RNA in a RNA:DNA duplex or at a site of direct or indirect RNA-DNA interaction, for example RNA at sites of RNA-DNA interaction in chromatin. In some embodiments, the RNA-degrading agent is an enzyme. In some embodiments, the RNA-degrading agent is a chemical or pharmaceutical compound.

In some embodiments, an enzyme that cuts or digests RNA in a sequence non-specific manner is used as an RNA-degrading agent. In some embodiments, the RNA-degrading enzyme is a sequence non-specific endoribonuclease, or "RNase." Any RNase that cleaves RNA may be used in the present invention. Examples of suitable RNases include, but are not limited to, RNase H (i.e., RNase H, RNase H1, and RNase H2) and RNase A. RNases used can include naturally occurring RNases, recombinant RNases, and modified RNases (e.g., RNases comprising mutations, insertions, or deletions). An example of a modified RNase is Hybridase™ Thermostable RNase H (Epicentre), which includes mutations that allow for greater thermostability.

In some embodiments, the RNA-degrading agent is a ribozyme. Ribozymes, which are enzymatic RNA molecules capable of catalyzing the specific cleavage of RNA, are known in the art. See, e.g., Heidenreich et al., *Nucleic Acids Res.*, 23:2223-2228 (1995). Ribozymes suitable for use in the present invention include both naturally occurring ribozymes or synthetic ribozymes.

Alternatively, the RNA-degrading agent may be any protein, small molecule, chemical, or drug that digests, cleaves, or degrades RNA in a RNA:DNA duplex or in a RNA-DNA interaction.

B. DNA-Degrading Agents

A DNA-degrading agent of the present invention is any reagent that is capable of cutting, digesting, or degrading single-stranded DNA, double-stranded DNA, or DNA in a RNA:DNA duplex or at a site of direct or indirect RNA-DNA interaction. In some embodiments, the DNA-degrading agent is an enzyme. In some embodiments, the DNA-degrading agent is a chemical or pharmaceutical compound.

In some embodiments, an enzyme that cuts or digests DNA, or "DNase," is used as a DNA-degrading agent. Any DNase that cleaves single-stranded DNA, double-stranded DNA, or DNA in a RNA:DNA duplex or RNA-DNA interaction may be used according to the present invention. DNases used can include naturally occurring DNases, recombinant DNases, and modified DNases (e.g., DNases comprising mutations, insertions, or deletions).

In some embodiments, the DNase is an enzyme that preferentially cleaves single-stranded DNA or DNA in a RNA:DNA duplex does not cleave double-stranded DNA or cleaves double-stranded DNA at only a very low level). Examples of suitable single-strand DNA-specific DNases include, but are not limited to, S1 nuclease, P1 nuclease, and mung bean nuclease.

In some embodiments, the DNase is an enzyme that cleaves double-stranded DNA but which also cleaves single-stranded DNA or DNA in a RNA:DNA duplex to a lesser extent. For these DNases, the amount of DNase that is required to cleave single-stranded DNA or DNA in a RNA:DNA duplex can be experimentally determined by one of skill in the art by titering the DNase. Examples of suitable double-strand DNA-specific DNases include, but are not limited to, DNase I and Bal 31 nuclease.

Alternatively, the DNA-degrading agent may be any protein, small molecule, chemical, or drug that digests, cleaves, or degrades single-stranded DNA, double-stranded DNA, or DNA in a RNA:DNA duplex or at a site of RNA-DNA interaction.

In some embodiments, the DNA-degrading agent (e.g., a DNase) degrades regions of genomic DNA, such as DNA in a RNA:DNA duplex or at a site of direct or indirect RNA-DNA interaction, due to the presence of an RNA-degrading agent (e.g., an RNase). In these embodiments, degradation of the RNA that is bound, associated with, or hybridized to genomic DNA results in the formation of single-stranded DNA or changes the local chromatin structure, thus making the DNA more or less accessible to the DNA degrading agent for degradation of the DNA. Whether degradation of genomic DNA by a DNA-degrading agent is due to the presence of an RNA-degrading agent can be experimentally determined by one of skill in the art. For example, a control experiment can be performed in which a genomic DNA is contacted by a DNA-degrading agent but not an RNA-degrading agent. The DNA regions that are degraded by the DNA-degrading agent in the "no RNA-degrading agent" control sample can be compared to the DNA regions that are degraded in a corresponding genomic DNA which has been contacted by both the DNA-degrading agent and an RNA-degrading agent, and those DNA regions which are degraded when RNA-degrading agent is present, but which are not degraded when RNA-degrading agent is absent, are the DNA regions that are degraded by the DNA-degrading agent due to the presence of the RNA-degrading agent.

IV. Permeabilizing and Disrupting Cells

Cell membranes can be permeabilized or disrupted in any way known in the art. According to the methods of the present invention, the membrane of a cell may be permeabilized or disrupted before or during the step of introducing the RNA-degrading agent and/or DNA-degrading agent to the cell.

In some embodiments, the cell membrane is contacted with an agent that permeabilizes or disrupts the cell membrane. Lysolipids are an exemplary class of agents that permeabilize cell membranes. Exemplary lysolipids include, but are not limited to, lysophosphatidylcholine (also known in the art as lysolecithin) or monopalmitoylphosphatidylcholine. A variety of lysolipids are also described in, e.g., WO/2003/052095.

Non-ionic detergents are an exemplary class of agents that disrupt cell membranes. Exemplary non-ionic detergents include, but are not limited to, NP40, Tween20, and Triton X-100.

Alternatively, electroporation or biolistic methods can be used to permeabilize a cell membrane such that a DNA modifying agent is introduced into the cell and can thus contact the genomic DNA. A wide variety of electroporation methods are well known and can be adapted for delivery of DNA modifying agents as described herein. Exemplary electroporation methods include, but are not limited to, those described in WO/2000/062855. Biolistic methods include but are not limited to those described in U.S. Pat. No. 5,179,022.

V. Detecting DNA after Degradation

In some embodiments, following RNA degradation and DNA degradation genomic DNA is isolated from the cells according to any method known in the art. Essentially any DNA purification procedure can be used so long as it results in DNA of acceptable purity for the subsequent detecting step(s). For example, standard cell lysis reagents can be used to lyse cells. Optionally a protease (including but not limited to proteinase K) can be used. DNA can be isolated from the mixture as is known in the art. In some embodiments, phenol/chloroform extractions are used and the DNA can be subsequently precipitated (e.g., by ethanol) and purified. Alternatively, DNA can be isolated on a nucleic-acid binding column.

Optionally, genomic DNA is amplified or otherwise detected directly from the cell lysate without an intermediate purification step.

A. Target DNA Region

Detection of DNA involves detecting the presence or absence of at least one DNA region in the genomic DNA. A DNA region is a target sequence of interest within genomic DNA. In some embodiments, a target DNA region is a region of genomic DNA to which RNA binds or hybridizes. Any DNA sequence in genomic DNA of a cell can be evaluated for RNA interaction as described herein.

Genomic DNA can be screened to identify a DNA region of interest that displays a different pattern or level of interaction with RNA in different cell types, for example, between untreated cells and cells exposed to a drug, chemical or environmental stimulus, or between normal and diseased tissue. Thus, in some embodiments, the methods of the invention are used to identify a DNA region whose change in pattern or level of RNA interaction acts as a marker for a disease, or lack thereof. Exemplary diseases include but are not limited to cancers. A number of genes have been described that have altered transcriptional activity and/or chromatin structure in cancer cells compared to non-cancer cells.

B. Detecting RNA Interaction with the Target DNA Region

A variety of methods can be used to detect and quantify the extent of RNA interaction with one or more target DNA regions. In some embodiments, detecting the one or more target DNA regions for RNA interaction involves detecting and quantifying the amount of target DNA region that is present. In some embodiments, detecting the one or more target DNA regions for RNA interaction involves detecting and quantifying a decrease in the number of copies of the target DNA region or detecting the absence of copies of the target DNA region.

As discussed below, quantitative amplification (including, but not limited to, real-time PCR) methods allow for determination of the amount of intact (i.e., non-degraded) copies of a DNA region, and can be used with various controls to determine the relative amount of intact copies of the DNA region in a sample of interest, thereby indicating whether and to what extent RNA is interacting with the DNA region. In such embodiments, a DNA region that is resistant or refractory to amplification would likely indicate degradation of the DNA region by the DNA-degrading agent, thereby indicating RNA interaction with the DNA region.

Quantitative amplification methods (e.g., quantitative PCR or quantitative linear amplification) involve amplification of nucleic acid template, directly or indirectly (e.g., determining a Ct value) determining the amount of amplified DNA, and then calculating the amount of initial template based on the number of cycles of the amplification. Amplification of a DNA locus using reactions is well known (see U.S. Pat. Nos. 4,683,195 and 4,683,202; PCR PROTOCOLS: A GUIDE TO METHODS AND APPLICATIONS (Innis et al., eds, 1990)). Typically, PCR is used to amplify DNA templates. However, alternative methods of amplification have been described and can also be employed, as long as the alternative methods amplify intact DNA to a greater extent than the methods amplify cleaved or degraded DNA. Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1):106-10, 112-5 (2003); Deiman B, et al., *Mol. Biotechnol.* 20(2):163-79 (2002). Amplifications can be monitored in "real time."

In some embodiments, quantitative amplification is based on the monitoring of the signal (e.g., fluorescence of a probe) representing copies of the template in cycles of an amplification (e.g., PCR) reaction. In the initial cycles of the PCR, a very low signal is observed because the quantity of the amplicon formed does not support a measurable signal output from the assay. After the initial cycles, as the amount of formed amplicon increases, the signal intensity increases to a measurable level and reaches a plateau in later cycles when the PCR enters into a non-logarithmic phase. Through a plot of the signal intensity versus the cycle number, the specific cycle at which a measurable signal is obtained from the PCR reaction can be deduced and used to back-calculate the quantity of the target before the start of the PCR. The number of the specific cycles that is determined by this method is typically referred to as the cycle threshold (Ct). Exemplary methods are described in, e.g., Heid et al. *Genome Methods* 6:986-94 (1996) with reference to hydrolysis probes.

One method for detection of amplification products is the 5'-3' exonuclease "hydrolysis" PCR assay (also referred to as the TaqMan™ assay) (U.S. Pat. Nos. 5,210,015 and 5,487,972; Holland et al., *PNAS USA* 88: 7276-7280 (1991); Lee et al., *Nucleic Acids Res.* 21: 3761-3766 (1993)). This assay detects the accumulation of a specific PCR product by hybridization and cleavage of a doubly labeled fluorogenic probe (the TaqMan™ probe) during the amplification reaction. The fluorogenic probe consists of an oligonucleotide labeled with both a fluorescent reporter dye and a quencher dye. During PCR, this probe is cleaved by the 5'-exonuclease activity of DNA polymerase if, and only if, it hybridizes to the segment being amplified. Cleavage of the probe generates an increase in the fluorescence intensity of the reporter dye.

Another method of detecting amplification products that relies on the use of energy transfer is the "beacon probe" method described by Tyagi and Kramer, *Nature Biotech.* 14:303-309 (1996), which is also the subject of U.S. Pat. Nos. 5,119,801 and 5,312,728. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in the open conformation and fluorescence is detected, while those that remain unhybridized will not fluoresce (Tyagi and Kramer, *Nature Biotechnol.* 14: 303-306 (1996)). As a result, the amount of fluorescence will increase as the amount of PCR product increases, and thus may be used as a measure of the progress of the PCR. Those of skill in the art will recognize that other methods of quantitative amplification are also available.

Various other techniques for performing quantitative amplification of nucleic acids are also known. For example, some methodologies employ one or more probe oligonucleotides that are structured such that a change in fluorescence is generated when the oligonucleotide(s) is hybridized to a target nucleic acid. For example, one such method involves is a dual fluorophore approach that exploits fluorescence resonance energy transfer (FRET), e.g., LightCycler™ hybridization probes, where two oligo probes anneal to the amplicon. The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: Scorpions™ probes (e.g., Whitcombe et al., *Nature Biotechnology* 17:804-807, 1999, and U.S. Pat. No. 6,326,145), Sunrise™ (or Amplifluor™) probes (e.g., Nazarenko et al., *Nuc. Acids Res.* 25:2516-2521, 1997, and U.S. Pat. No. 6,117,635), and probes that form a secondary structure that results in reduced signal without a quencher and that emits increased signal when hybridized to a target (e.g., Lux Probes™).

In some embodiments, intercalating agents that produce a signal when intercalated in double stranded DNA may be used. Exemplary agents include SYBR GREEN™, SYBR GOLD™, and EVAGREEN™. Since these agents are not template-specific, it is assumed that the signal is generated based on template-specific amplification. This can be confirmed by monitoring signal as a function of temperature because melting point of template sequences will generally be much higher than, for example, primer-dimers, etc.

In some embodiments, the number of copies of a DNA region is compared to a control value. Control values can be conveniently used, for example, where one wants to know whether the number of copies of intact (i.e., non-degraded and therefore non-RNA-interacting) DNA region exceeds or is under a particular value. For example, in the situation where a particular DNA region typically does not interact with an RNA in normal cells, but does interact with the RNA in diseased cells (or vice versa), one may simply compare the number of intact copies of the DNA region to a control value.

In some embodiments, a DNA region that interacts with RNA is identified or detected by sequencing. For example, a genomic DNA sequence for a sample of interest can be sequenced and compared to corresponding known genomic DNA sequences in order to determine sites of DNA degradation in the sample of interest. In such embodiments, a site of DNA degradation in the sample of interest (e.g., a DNA region that is absent in the sample of interest but present in the corresponding known genomic DNA sequence) is indicative of a region of RNA-DNA interaction. Methods of nucleic acid sequencing are well-known in the art. Examples of sequence analysis include, but are not limited to, Maxam-Gilbert sequencing, Sanger sequencing, capillary array DNA sequencing, thermal cycle sequencing (Sears et al., *Biotechniques,* 13:626-633 (1992)), solid-phase sequencing (Zimmerman et al., *Methods Mol. Cell Biol.,* 3:39-42 (1992)), sequencing with mass spectrometry such as matrix-assisted laser desorption/ionization time-of-flight mass spectrometry (MALDI-TOF/MS; Fu et al., *Nature Biotech.,* 16:381-384 (1998)), and sequencing by hybridization (Chee et al., *Science,* 274:610-614 (1996); Drmanac et al., *Science,* 260: 1649-1652 (1993); Drmanac et al., *Nature Biotech.,* 16:54-58 (1998)).

In some embodiments, an RNA-interacting target DNA region, or a larger genomic DNA sequence comprising the target DNA region, is isolated and cloned into a library. In some cases, one or more target DNA regions, or one or more genomic DNA sequences comprising one or more target DNA regions, is isolated and/or cloned. Alternatively, a sample having one or more target DNA regions is used to prepare a library enriched for such regions. In such embodiments, a target DNA region, or a larger genomic DNA sequence comprising the target DNA region, is purified (e.g., separated) from non-target DNA regions prior to cloning, thereby enriching the cloning pool for one class of DNA.

In some embodiments, subtractive libraries are generated. For example, libraries can be generated that are enriched for RNA-interacting target DNA regions in a diseased cell and subsequently subtracted with a corresponding library from a healthy cell, thereby generating a library of differential DNA sequences that both comprise the RNA-interacting target DNA region and are specific for the particular disease. Any diseased cell can be used, including but not limited to, cancer cells. Alternate subtractive strategies can also be employed, e.g., between different cell types, cell stages, drug treatments, etc.

In some embodiments, RNA interaction with a DNA region is detected by size selection. This is useful, for example, to enrich for regions that interact with RNA (i.e., shorter fragments) or those regions that do not interact with RNA (larger fragments or intact regions). This is useful, for example, in generating populations of nucleic acids that are enriched for DNA regions that interact (or those that do not) with RNA. Alternatively, size selection can be performed to assist in detection of particular DNA region(s). Where the DNA region of interest is known, size fractionation or size selection can be used to detect whether there is degradation of the sequence (e.g., by detecting whether DNA fragments are intact and relatively longer or fragmented and relatively shorter). For example, in some embodiments, DNA is isolated for a section of genomic DNA comprising the DNA region of interest (or from a library enriched for the section of genomic DNA comprising the DNA region of interest) and subjected to size separation according to any known method. Examples of nucleic acid size separation techniques include, but are not limited to, agarose gel electrophoresis (e.g., Quertermous, Curr. Protoc. Mol. Biol., Chapter 5:Unit 5.4 (May 2001)) and sucrose gradient (e.g., Weis and Quertermous, Curr. Protoc. Mol. Biol., Chapter 5:Unit 5.3 (May 2001)).

In such embodiments, the presence or absence of degradation at the DNA region may be determined by detecting for the fractionation of the DNA sequence into smaller segments, which indicates degradation of a DNA region within that larger DNA sequence. The presence of fragmented or relatively shorter DNA fragments indicates the presence of RNA-interacting regions in that DNA sequence, while the presence of intact or relatively longer DNA fragments indicates the relative absence of RNA-interacting regions in that DNA sequence. "Relative absence," as used herein, refers to a reduced extent of RNA interaction in a DNA region relative to a normal control or to a level of RNA interaction in a DNA region that is below a threshold detection level.

In some embodiments, RNA-interacting DNA region are identified using a tiling array. Chip-based tiling arrays which allow for screening of an entire genome or portions thereof are known in the art and are commercially available (e.g., Roche NimbleGen Whole-Genome Tiling Array or Targeted-Tiling Array, Madison, Wis.). For example, in some embodiments, following RNA degradation and DNA degradation genomic DNA is isolated and amplified according to known methods. Amplified products are end-labeled (e.g., using a fluorescent label) to indicate DNA regions that border sites of RNA-DNA interaction, then incubated with a tiling array according to the manufacturer's instructions in order to hybridize the samples to nucleic acid on the array. The identity of the DNA region that interacts with RNA can be determined by determining the nucleic acid sequence on the tiling array where hybridization occurred, while the label indicates the location in the nucleic acid sequence where RNA-DNA interaction occurred.

In some embodiments, a select number of DNA regions are analyzed by the methods of the present invention. Alternatively, a genome-wide map of RNA-DNA interactions can be created. Without intending to limit the invention to a particular use, it is believed that a select number of regions will be examined in situations where RNA interaction with a DNA region is known to have a particular association, e.g., with a disease or cell phenotype, whereas a genome-wide assessment will be made where it is desired to identify regions of interest that differ between two treatments, cell types, phenotypes, diseases, etc.

The calculations for the methods described herein can involve computer-based calculations and tools. The tools are advantageously provided in the form of computer programs that are executable by a general purpose computer system (referred to herein as a "host computer") of conventional design. The host computer may be configured with many different hardware components and can be made in many dimensions and styles (e.g., desktop PC, laptop, tablet PC, handheld computer, server, workstation, mainframe). Standard components, such as monitors, keyboards, disk drives, CD and/or DVD drives, and the like, may be included. Where the host computer is attached to a network, the connections may be provided via any suitable transport media (e.g., wired, optical, and/or wireless media) and any suitable communication protocol (e.g., TCP/IP); the host computer may include suitable networking hardware (e.g., modem, Ethernet card, WiFi card). The host computer may implement any of a variety of operating systems, including UNIX, Linux, Microsoft Windows, MacOS, or any other operating system.

Computer code for implementing aspects of the present invention may be written in a variety of languages, including PERL, C, C++, Java, JavaScript, VBScript, AWK, or any other scripting or programming language that can be executed on the host computer or that can be compiled to execute on the host computer. Code may also be written or distributed in low level languages such as assembler languages or machine languages.

The host computer system advantageously provides an interface via which the user controls operation of the tools. In the examples described herein, software tools are implemented as scripts (e.g., using PERL), execution of which can be initiated by a user from a standard command line interface of an operating system such as Linux or UNIX. Those skilled in the art will appreciate that commands can be adapted to the operating system as appropriate. In other embodiments, a graphical user interface may be provided, allowing the user to control operations using a pointing device. Thus, the present invention is not limited to any particular user interface.

Scripts or programs incorporating various features of the present invention may be encoded on various computer readable media for storage and/or transmission. Examples of suitable media include magnetic disk or tape, optical storage media such as compact disk (CD) or DVD (digital versatile disk), flash memory, and carrier signals adapted for transmission via wired, optical, and/or wireless networks conforming to a variety of protocols, including the Internet.

VI. Diagnostic and Prognostic Methods

The present invention also provides methods for diagnosing or providing a prognosis for a disease or condition or determining a course of treatment for a disease or condition based on the detection of RNA-interaction regions in genomic DNA.

In some embodiments, RNA interaction with a DNA region of interest is increased (or at least is present) or decreased (or absent) in a diseased cell or tissue as compared to a normal (i.e., non-diseased) cell or tissue. In these embodiments, the methods of the present invention to detect the presence or absence of the DNA region of interest can be used as a diagnostic or prognostic tool. For example, in some embodiments, RNA interaction with a target DNA region may not occur in a normal cell or tissue, whereas RNA interaction with the target DNA region is increased in a diseased (e.g., cancerous) cell or tissue. By introducing an RNA-degrading agent and a DNA-degrading agent to the normal and diseased cells or tissues, and subsequently detecting the extent of degradation of the target DNA region in the normal and diseased cells or tissues, it is possible to compare the differential RNA interaction between the normal and diseased cells or tissues. In these embodiments, increased RNA interaction with the target DNA region in the diseased cell or tissue is expected to result in increased degradation of the target DNA region, and therefore a decreased number of copies of the DNA region will be detectable for the diseased cell or tissue, or the number of copies of the DNA region will be sufficiently low as to be undetectable for the diseased cell or tissue, as compared to the normal cell or tissue.

Alternatively, in some embodiments, RNA interaction with a target DNA region may occur in a normal cell or tissue, whereas RNA interaction with the target DNA region is decreased or absent in a diseased cell or tissue. In these embodiments, decreased or absent RNA interaction with the target DNA region in the diseased cell or tissue is expected to result in decreased degradation of the target DNA region, and therefore an increased number of copies of the DNA region will be detectable for the diseased cell or tissue as compared to the normal cell or tissue.

Once a diagnosis or prognosis is established using the methods of the invention, a regimen of treatment can be established or an existing regimen of treatment can be altered in view of the diagnosis or prognosis. For instance, detection of a cancer cell according to the methods of the invention can lead to the administration of chemotherapeutic agents and/or radiation to an individual from whom the cancer cell was detected.

A variety of DNA regions can be detected either for research purposes and/or as a control DNA region to confirm that the reagents were performing as expected. For example, in some embodiments, a DNA region is assayed that is known to interact with RNA, for example, an inactivated X chromosome in female cells that is known to interact with Xist RNA.

Such DNA regions are useful, for example, as positive controls for RNA-DNA interaction.

VII. Kits

The present invention also provides kits for performing the RNA interaction assays of the present invention. A kit can optionally include written instructions or electronic instructions (e.g., on a CD-ROM or DVD). Kits of the present invention can include, e.g., an RNA-degrading agent, a DNA-degrading agent. In some embodiments, the kits further comprise a cell permeabilizing and/or cell disrupting agent. RNA-degrading agents and DNA-degrading agents can include those described herein in detail, e.g., enzymes, proteins, chemicals, pharmaceutical compounds, and small molecules that degrade RNA or DNA in a RNA:DNA duplex or single-stranded DNA. In some embodiments, the RNA-degrading agent is an RNase, e.g., RNase H. In some embodiments, the DNA-degrading agent is a DNase, e.g., S1 nuclease. Kits of the invention can comprise the RNA-degrading agent, the DNA-degrading agent, and permeabilizing agent in the same vial/container (and thus in the same buffer). Alternatively, one or more of the RNA-degrading agent, the DNA-degrading agent, and permeabilizing agent can be in a separate vial/container.

The kits of the invention can also include one or more control cells and/or nucleic acids. In some embodiments, the kits include one or more sets of primers for amplifying such genomic sequences (whether or not the actual genomic sequences or cells are included in the kits). For example, in some embodiments, the kits include an RNA-degrading agent, a DNA-degrading agent, a cell permeabilizing and/or cell disrupting agent, and one or more primer sets for amplifying a control DNA region, and optionally one or more primer sets for amplifying a second DNA region, e.g., a target DNA region. In some embodiments, the kits further comprise materials for the isolation of DNA. Such materials include, but are not limited to, "stop" solutions capable of preventing further degradation by the RNA-degrading agent and/or DNA-degrading agent, spin columns for purification of genomic DNA and/or removal of non-DNA components such as components of a "stop" solution, and buffers.

In some embodiments, the kits of the invention comprise one or more of the following:

(i) a cell membrane permeabilizing or disrupting agent;

(ii) a RNA-degrading agent;

(iii) a DNA-degrading agent;

(iv) a "stop" solution capable of preventing further degradation by the RNA-degrading agent and/or DNA-degrading agent;

(v) materials for the isolation of nucleic acids (e.g., spin columns)

(vi) reagents for PCR/qPCR amplification of DNA, optionally one mixture containing all components necessary for PCR or for qPCR aside from the template and/or polymerase;

(vii) primer sets for PCR/qPCR amplification of specific target DNA regions.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of detecting RNA-interacting regions in genomic DNA, the method comprising:

introducing an RNA-degrading agent and a DNA-degrading agent into a nucleus, whereby at least one DNA region in the genomic DNA is degraded by the DNA-degrading agent due to the presence of the RNA-degrading agent;

detecting the at least one DNA region in the genomic DNA that is degraded by the DNA-degrading agent; and comparing the amount of the at least one DNA region that is detected to a control sample in which the genomic DNA is contacted by the DNA-degrading agent but not the RNA-degrading agent, wherein an absence or reduction in the quantity of copies of a DNA region, relative to the control sample, indicates that the DNA region is degraded by the DNA-degrading agent; thereby detecting the RNA-interacting regions.

2. The method of claim 1, wherein the DNA-degrading agent is a single-stranded DNA-degrading agent.

3. The method of claim 1, wherein the DNA-degrading agent is a double-stranded DNA-degrading agent.

4. The method of claim 1, wherein the DNA-degrading agent is an agent that degrades an RNA:DNA duplex.

5. The method of claim 1, wherein the nucleus is in a cell and the RNA-degrading agent and the DNA-degrading agent are introduced into the cell.

6. The method of claim 5, comprising permeabilizing or disrupting a cell membrane of the cell before or during the introducing step, thereby enhancing introduction of the RNA-degrading agent and/or the DNA-degrading agent into the cell.

7. The method of claim 1, wherein the RNA-degrading agent and/or the DNA-degrading agent is a protein.

8. The method of claim 7, wherein the RNA-degrading agent and/or the DNA-degrading agent is encoded by a heterologous expression cassette in the cell and the introducing step comprises expressing the agent in the cell.

9. The method of claim 1, wherein the nucleus is an isolated nucleus and the introducing step comprises introducing the RNA-degrading agent and the DNA-degrading agent into the isolated nucleus.

10. The method of claim 1, wherein the RNA-degrading agent is introduced into the nucleus before the DNA-degrading agent is introduced into the nucleus.

11. The method of claim 1, wherein the RNA-degrading agent and the DNA-degrading agent are introduced into the nucleus simultaneously.

12. The method of claim 1, wherein the RNA-degrading agent is an RNase.

13. The method of claim 12, wherein the RNase is RNase H.

14. The method of claim 1, wherein the DNA-degrading agent is a DNase.

15. The method of claim 14, wherein the DNase is S1 nuclease.

16. The method of claim 14, wherein the DNase is DNase I.

17. The method of claim 1, wherein the detecting step comprises nucleotide sequencing or hybridizing a nucleic acid to the at least one DNA region in the genomic DNA that is not degraded.

18. The method of claim 1, wherein the detecting step comprises DNA amplification of the at least one DNA region, wherein a region that is refractory to amplification is likely degraded by the DNA-degrading agent.

19. The method of claim 18, wherein the DNA amplification comprises a polymerase chain reaction (PCR).

20. The method of claim 1, wherein the genomic DNA is fragmented by the DNA-degrading agent and the method further comprises enriching the DNA for either intact or fragmented DNA and/or size selecting the DNA, wherein intact or relatively larger DNA fragments indicate the relative absence of RNA-interacting regions in the DNA and wherein fragmented or relatively smaller DNA fragments indicate the presence of RNA-interacting regions in the DNA.

* * * * *